(12) United States Patent
Dotsch et al.

(10) Patent No.: US 7,776,261 B2
(45) Date of Patent: Aug. 17, 2010

(54) AQUEOUS SOLUTION FOR THE CHEMICAL STERILIZATION OF PACKAGING MATERIALS, PROCESS FOR ITS PREPARATION AND ITS USE

(75) Inventors: Werner Dotsch, Linz Am Rhein (DE); Otmar Woost, Bernburg (DE)

(73) Assignee: Solvay (Societe Anonyme), Brussels (BE)

( * ) Notice: Subject to any disclaimer, the term of this patent is extended or adjusted under 35 U.S.C. 154(b) by 4 days.

(21) Appl. No.: 12/065,336

(22) PCT Filed: Sep. 8, 2006

(86) PCT No.: PCT/EP2006/066180

§ 371 (c)(1),
(2), (4) Date: Feb. 29, 2008

(87) PCT Pub. No.: WO2007/031471

PCT Pub. Date: Mar. 22, 2007

(65) Prior Publication Data

US 2008/0226497 A1 Sep. 18, 2008

(30) Foreign Application Priority Data

Sep. 12, 2005 (EP) .................. 05108331

(51) Int. Cl.
*A61L 2/18* (2006.01)
(52) U.S. Cl. ........................ 422/28; 424/616
(58) Field of Classification Search .............. None
See application file for complete search history.

(56) References Cited

U.S. PATENT DOCUMENTS

| 4,424,189 | A | * | 1/1984 | Hick | 422/27 |
| 4,879,043 | A | * | 11/1989 | Boughton et al. | 210/651 |
| 5,232,680 | A | * | 8/1993 | Honig et al. | 423/584 |
| 5,720,983 | A | | 2/1998 | Malone | |
| 5,817,253 | A | * | 10/1998 | Grimberg et al. | 252/186.29 |
| 6,406,666 | B1 | | 6/2002 | Cicha et al. | |
| 2004/0247755 | A1 | * | 12/2004 | Doetsch et al. | 426/392 |
| 2005/0239679 | A1 | | 10/2005 | Doetsch et al. | |

FOREIGN PATENT DOCUMENTS

| DE | 19945500 A1 | 4/2000 |
| EP | 0342485 A1 | 11/1989 |
| EP | 0930269 A1 | 7/1999 |
| EP | 1050467 A1 | 11/2000 |
| EP | 1197432 A1 | 4/2002 |
| WO | WO99/21593 A1 | 5/1999 |
| WO | WO2005033005 A1 | 4/2005 |

OTHER PUBLICATIONS

European Chemical Industry Council, CEFIC Peroxygens H2O2 AM-7157, "Hydrogen Peroxide For Industrial Use Determination of Hydrogen Peroxide Content Titrimetric Method", Mar. 2003, pp. 1-8.
International Organization For Standardization, International Standard ISO/DIS 7161 (draft version), Hydrogen Peroxide For Industrial Use-Stability Test-Determination of Percentage Loss of Hydrogen Peroxide After 16 h at 96° C, 1996, pp. 1-4.
International Electrotechnical Commission, International Standard IEC 060746-1:2003(E), "Expression of Performance of Electrochemical Analyzers," Jan. 2003, Second Edition, pp. 1-23.
Unknown, "Hydrogen Peroxide" in Kirk-Othmer Encyclopedia of Chemical Technology, 3rd Edition, (1981) vol. 13 : Hydrogen-Ion Activity to Laminated Materials, Glass, John Wiley and Sons, Inc., New York, pp. 16-21.

* cited by examiner

*Primary Examiner*—Elizabeth L McKane
(74) *Attorney, Agent, or Firm*—Beatrice C. Ortego

(57) ABSTRACT

Aqueous solution suitable for the chemical sterilization of packaging materials, process for its preparation and its use Aqueous solution suitable for the chemical sterilization of packaging materials, comprising hydrogen peroxide and at least one foodstuff-compatible stabilizer. This solution but without the stabilizer has a maximum phosphorous content expressed as $PO_4^{3-}$ —of 10 mg/kg, and present a dry residue at 105° C. of at most 10 mg/kg. The same solution can be used as dip bath liquid in dip bath aseptic packaging processes and as well as spraying liquid in spray aseptic packaging processes.

14 Claims, No Drawings

AQUEOUS SOLUTION FOR THE CHEMICAL STERILIZATION OF PACKAGING MATERIALS, PROCESS FOR ITS PREPARATION AND ITS USE

CROSS REFERENCE TO RELATED APPLICATIONS

The present application claims the benefit of the European patent application 05108331.9 filed Sep. 12, 2005, herein incorporated by reference.

The present invention is related to aqueous solutions suitable for the chemical sterilization of packaging materials, especially those containing hydrogen peroxide. It is also related to a process for the preparation of these aqueous solutions and to their use for the chemical sterilization of packaging materials.

It is known to use hydrogen peroxide solutions for the chemical sterilization of packaging materials. Two such aseptic packaging processes exist. The first is a dip bath packaging process, in which the packaging materials are dipped in the hydrogen peroxide solution, such as described for instance in the European patent application EP 0342485. The sterilization in such processes is usually operated at a high temperature of typically 80° C. In order to prevent that the hydrogen peroxide decomposes at this high temperature, a high amount of stabilizer must be present in the sterilizing solution.

The second aseptic packaging process is a spray packaging process, in which the packaging materials are purged with a hydrogen peroxide solution, such as described for instance in the German patent application DE 19945500. The hydrogen peroxide solutions used in these processes must have a very low dry residue in order to prevent incrustations in the evaporator or spraying section and to avoid thereby frequent cleaning. The dry residues can, amongst others, originate from the stabilizers present in the $H_2O_2$ solution. Thus, the spray technology requires a low amount of stabilizer.

Up to now it has therefore been unavoidable to use two different hydrogen peroxide solutions for the two processes. This forces the users of packaging machines, who have most often both processes on site, to dispose of two different storage facilities with the possibility of mistake when taking one of the two products.

In an attempt to develop one single hydrogen peroxide solution which could be used in both spray and dip bath processes, the United States patent application US 2004/0247755 of SOLVAY INTEROX GmbH proposes a new foodstuff-compatible stabilizer, i.e. aminotrismethylene phosphonic acid. This stabilizer can effectively be used in low amounts, especially in the dip bath processes. However, the dry residue of these $H_2O_2$ solutions is still too high in order to be also suitable in the spray technology.

The purpose of the present invention consists in developing a new hydrogen peroxide solution which can be used for the chemical sterilization of packaging materials in both dip bath and spray processes and which has the following features:
- it is safe
- it fits with pharmacopoeia standards
- it does not contain harmful contaminants such as anthraquinones coming for the auto-oxidation process for the manufacture of hydrogen peroxide
- it avoids incrustations or deposits in heater blocks of the spray process equipment or on the rubber rollers of the bath process equipment
- it is stable for transport and storage
- it meets legal requirements for food grade quality or any other regulation that applies
- it is stable for at least 120 h during operation
- it contains a stabilizer which is soluble in water or in dilute acids for easy cleaning and maintaining of the packaging machines.

To this end, the present invention concerns an aqueous solution suitable for the chemical sterilization of packaging materials, comprising hydrogen peroxide and at least one foodstuff-compatible stabilizer, wherein the said solution but without the foodstuff-compatible stabilizer has a maximum phosphorous content expressed as $PO_4^{3-}$ of 10 mg/kg, and presents a dry residue at 105° C. of at most 10 mg/kg.

One of the characteristic features of the present invention resides in the use of a foodstuff-compatible stabilizer preferably in a sufficiently low amount, combined with a low amount of impurities present in the solution before addition of the foodstuff-compatible stabilizer, in order to yield a low dry residue. This combination has made it possible to provide one single hydrogen peroxide solution which can be used in both aseptic packaging processes which are the dip bath and the spray processes.

The aqueous solution of the present invention but without the foodstuff-compatible stabilizer has a maximum phosphorous content expressed as $PO_4^{3-}$ of 10 mg/kg. This content is often lower than or equal to 8 mg/kg. In most cases it is lower than or equal to 5 mg/kg. It is preferably lower than or equal to 2.5 mg/kg. Generally, it is higher than or equal to 0.1 mg/kg. The phosphorous content is measured by the well known ICP-method.

The aqueous solution of the present invention (including the foodstuff-compatible stabilizer) generally has a maximum phosphorous content expressed as $PO_4^{3-}$ of 10 mg/kg. This content is preferably lower that or equal to 8. mg/kg. In most cases, it is higher than or equal to 0.1 mg/kg.

The aqueous solution of the invention has a maximum chloride content of 1 mg/kg. This content is often lower than or equal to 0.75 mg/kg. In most cases it is lower than or equal to 0.5 mg/kg. It is preferably lower than or equal to 0.1 mg/kg, and most preferably lower than or equal to 0.05 mg/kg. Generally, it is higher than or equal to 0.001 mg/kg.

The aqueous solution of the invention but without the feedstuff-compatible stabilizer presents a dry residue at 105° C. of at most 10 mg/kg, generally at most 7 mg/kg, and preferably at most 5 mg/kg. This dry residue is often higher than or equal to 0.1 mg/kg, in particular higher than or equal to 0.5, and in many cases at least 1 mg/kg. The dry residue is measured on the solution before addition of the foodstuff-compatible stabilizer, by the gravimetric method according to the following procedure:
1. Place a platinum dish in a muffle furnace at 900° C. for 1 h.
2. Cool the dish in a dessicator and then weigh to the nearest 0.0001 g; let this weight be B, g.
3. Weigh to the nearest 0.0001 g a 100 ml beaker and record the weight; add to this beaker:
   100 g of sample (if the $H_2O_2$ concentration is 50% or lower)
   50 g of sample (if the $H_2O_2$ concentration is higher than 50%).
4. Reweigh the beaker to the nearest 0.0001 g. The weight difference of the beaker before and after the sample addition will be W, g.
5. Dilute the sample to approximately 100 ml with demineralised water if using 50 g of sample.
6. Transfer progressively and carefully the sample into a platinum evaporating dish, surrounded by cold water. If the dish is extremely clean (it will be shiny), it would be iced down. Caution must be taken: the decomposition of hydrogen peroxide is accompanied by the production of substantial amount of heat and gas formation; sample must be added carefully, in small portions, with adequate cooling.
7. Evaporate the solution carefully until dry, on the steam bath. Caution must be taken: failure to completely decompose the hydrogen peroxide prior to evaporation could concentrate the sample sufficiently to produce an explosion hazard.
8. Place the dish in an oven at 105° C. for at least 1 hour.
9. Cool in a dessicator for 30 minutes and weigh the dish to the nearest 0.0001 g. Let this weight be A, g.
10. Calculate the residue at 105° C. using the equation:

$$\text{Residue at } 105° \text{ C., g/kg} = \frac{A - B}{W} \times 1000$$

Where:
A (in g) is the weight of the dish containing the evaporation residue
B (in g) is the weight of the empty dish
W (in g) is the weight of the sample added to the dish.

The aqueous solution of the invention (including the foodstuff-compatible stabilizer) presents a dry residue at 105° C., measured according to the procedure above, of at most 10 mg/kg, preferably at most 7 mg/kg. This dry residue is often higher than or equal to 0.1 mg/kg, and most often higher than or equal to 0.5 mg/kg.

The aqueous solution of the invention generally presents a conductivity of from 20 to 150 μS/cm, particularly from 50 to 90 μS/cm. The conductivity is measured according to the method of the standard DIN IEC 60746-1. The conductivity of the aqueous solution can de adjusted by the addition therein of a salt, such as for instance ammonium nitrate or mineral acid.

The aqueous solution of the invention usually presents a hydrogen peroxide concentration of from 10 to 50% wt. in particular from 20 to 45% wt, most preferably from 30 to 40% wt, typically of about 35% wt. The hydrogen peroxide concentration is measured according to the ISO standard 7157 (draft version).

The aqueous solution of the invention usually presents a maximum acidity of 5 mmol/kg.

The aqueous solution of the invention contains a foodstuff-compatible stabilizer. This stabilizer can be chosen from foodstuff-compatible phosphonic acids. An example is the aminotrismethylene phosphonic acid described in the patent application US 2004/0247755 the content of which is incorporated herein by reference. The amount of stabilizer is generally at least 0.5 mg (100% stabilizer) per kg of $H_2O_2$ solution, in particular at least 1 mg per kg $H_2O_2$ solution. The amount is usually lower than or equal to 50 mg (100% stabilizer) per kg of $H_2O_2$ solution, especially lower than or equal to 10 mg per kg of $H_2O_2$ solution, and preferably lower than or equal to 8 mg per kg of $H_2O_2$ solution. The amount is for instance about 5 mg (100% stabilizer) per kg of $H_2O_2$ solution. The stabilizer can be used in the form of an aqueous solution, for instance containing 50% wt of stabilizer.

Due to the presence of the stabilizer, the hydrogen peroxide concentration in the aqueous solution of the invention presents a high stability. It is usually so that the relative percentage of titration loss after 16 h at 96° C. is lower than or equal to 5% of the initial hydrogen peroxide concentration. The stability is measured according to the method of the ISO standard 7161 (draft version).

The aqueous solution of the present invention can be prepared by any adequate method which allows to prepare an aqueous solution of hydrogen peroxide and to purify it to such an extent that the dry residue is such as described above, and by adding thereto a foodstuff-compatible stabilizer in a low enough quantity so that the dry residue is as described above.

A possible process for the preparation of a hydrogen peroxide solution consists in the well known auto-oxidation process using anthraquinones, hydrogen and oxygen such as described in the Kirk-Othmer Encyclopedia of Chemical Technology, 1981, $3^{rd}$ Edition, vol 13, pages 16-21.

A possible process for the purification of the so obtained hydrogen peroxide solution consists in treating the hydrogen peroxide solution by reverse osmosis using a membrane. Examples can be found in the patent applications EP 0930269 and WO2005/033005 owned by SOLVAY (Société Anonyme).

The invention therefore also concerns a process for the preparation of the aqueous solution described above, wherein the hydrogen peroxide solution, before adding thereto the stabilizer, is purified by reverse osmosis using a membrane.

The aqueous solution of the invention can advantageously be used for the chemical sterilization of packaging materials. The invention is therefore also related to the use of the aqueous solution described above for the chemical sterilization of packaging materials.

One of the advantages of the aqueous solution of the invention resides in the fact that the same solution can be used as dip bath liquid in dip bath aseptic packaging processes as well as spraying liquid in spray aseptic packaging processes.

Another advantage resides in the high stability of the aqueous solution of the invention especially when it is used in dip bath aseptic packaging processes. This stability is expressed as follows: the hydrogen peroxide concentration does not differ in most cases from the initial value by more than 10% during at least 120 h of operation.

Due to the low stabilizer content, the risk of incrustations and blockages in the heaters of a spray packaging machine is minimized.

The invention is further described by way of illustration in the following examples.

EXAMPLES

A non-purified hydrogen peroxide solution was prepared according to the auto-oxidation process and followed by a distillation. The final product presented the following features:

| | |
|---|---|
| $H_2O_2$ concentration: | 35% w/w |
| Trace metals: | |
| Al | <0.1 ppm |
| Cr | 0.03 ppm |
| Fe | 0.12 ppm |
| Ni | 0.02 ppm |
| Cl | 0.1 ppm |
| $SO_4^{2-}$ | 0.1 ppm |
| P as $PO_4^{3-}$ | 17.3 ppm |
| Total Organic Carbon (TOC): | 50 ppm |
| Dry residue: | 25 ppm |

This solution was then purified by reverse osmosis using a membrane of the type SWC 3, supplied by the company HYDRANAUTICS, at a pressure of about 28 bar. The final purified product presented the following features:

| | |
|---|---|
| H₂O₂ concentration: | 35% w/w |
| Trace metals: | |
| Al | <0.005 ppm |
| Cr | <0.002 ppm |
| Fe | <0.005 ppm |
| Ni | <0.002 ppm |
| Cl | <0.005 ppm |
| $SO_4^{2-}$ | <0.05 ppm |
| P as $PO_4^{3-}$ | <1 ppm |
| TOC: | <5 ppm |
| Dry residue: | <2 ppm |

Then, aminotrismethylene phosphonic acid was added as stabilizer in an amount of 10 mg in the form of a 50% wt aqueous solution per kg of H₂O₂ solution, trade name CUBLEN API (manufacturer ZSCHIMMER & SCHWARZ, MOHSDORF GmbH & Co KG).

This stabilized aqueous H₂O₂ solution were successively used in dip bath aseptic packaging machines of the type TBA 8, TBA 9, TBA 19 and TBA 21, as well as in spray aseptic packaging machines of the company COMBIBLOC. Both types of machines have been operated for at least 120 h without losing performance.

The invention claimed is:

1. An aqueous solution suitable for the chemical sterilization of packaging materials, comprising hydrogen peroxide and at least one foodstuff-compatible stabilizer, wherein said aqueous solution without the foodstuff-compatible stabilizer has a maximum phosphorous content expressed as $PO_4^{3-}$ of 10 mg/kg, and presents a dry residue at 105° C. of at most 5 mg/kg.

2. The aqueous solution according to claim 1, presenting a conductivity of from 50 to 90 µS/cm.

3. The aqueous solution according to claim 1, presenting a hydrogen peroxide concentration of from 35 to 40% wt.

4. The aqueous solution according to claim 1, wherein the hydrogen peroxide concentration presents a high stability expressed as a relative percentage of titration loss after 16 hours at 96° C. of maximum 5%.

5. The aqueous solution according to claim 1, presenting a maximum acidity of 5 mmol/kg.

6. The aqueous solution according to claim 1, wherein the foodstuff-compatible stabilizer is a phosphonic acid.

7. The aqueous solution according to claim 1, containing from 0.5 to 50 mg per kg H₂O₂ solution of the foodstuff-compatible stabilizer.

8. A process for the preparation of the aqueous solution of claim 1, wherein the hydrogen peroxide solution, before adding thereto the stabilizer, is purified by reverse osmosis using a membrane.

9. The aqueous solution according to claim 1, wherein said aqueous solution without the foodstuff-compatible stabilizer has a dry residue at 105° C. of less than 2 ppm.

10. The aqueous solution according to claim 1, wherein the foodstuff-compatible stabilizer is a aminotrismethylene phosphonic acid.

11. The aqueous solution according to claim 1, containing from 1 to 10 mg per kg H₂O₂ solution of the foodstuff-compatible stabilizer.

12. A method for the chemical sterilization of packaging materials comprising using the aqueous solution of claim 1 by dipping a packaging material in said aqueous solution or spraying a packaging material with said aqueous solution.

13. The method according to claim 12, wherein the same aqueous solution is used as dip bath liquid in dip bath aseptic packaging processes as well as spraying liquid in spray aseptic packaging processes.

14. The method according to claim 12, wherein the aqueous solution is used in a dip bath aseptic packaging process, and wherein the hydrogen peroxide concentration does not differ from the initial value by more than 10% during at least 120 hours of operation.

* * * * *